United States Patent [19]

Lehnert et al.

[11] Patent Number: 5,154,088
[45] Date of Patent: Oct. 13, 1992

[54] APPARATUSES AND METHODS FOR INCORPORATING BLOWING AGENTS INTO LIQUIDS FOR THE PRODUCTION OF POLYMER FOAMS AND FOR MEASURING THE VOLUMETRIC EXPANSION POTENTIAL OF MIXTURES THEREOF

[75] Inventors: Andrew B. Lehnert, Copley; Mark S. Hoenke, Stow, both of Ohio; Henri J. M. Gruenbauer, Oostburg, Netherlands

[73] Assignee: The Dow Chemical Company, Midland, Mich.

[21] Appl. No.: 710,213

[22] Filed: Jun. 4, 1991

Related U.S. Application Data

[63] Continuation-in-part of Ser. No. 558,086, Jul. 24, 1990, Pat. No. 5,119,668.

[51] Int. Cl.⁵ .............................................. G01N 7/00
[52] U.S. Cl. ...................................... 73/866; 73/19.1; 521/133
[58] Field of Search ............... 73/38, 866, 53, 19.1; 521/133

[56] References Cited

U.S. PATENT DOCUMENTS

| | | | |
|---|---|---|---|
| 3,063,952 | 11/1962 | Vieli | 260/2.5 |
| 3,096,001 | 7/1963 | Boe et al. | 222/135 |
| 3,170,972 | 2/1965 | Knipp et al. | 264/176 |
| 3,188,296 | 6/1965 | Hoppe et al. | 260/2.5 |
| 3,488,300 | 1/1970 | Burkholder et al. | 260/2.5 |
| 3,769,232 | 10/1973 | Houldridge | 232/359 |
| 3,882,052 | 5/1975 | Raynor et al. | 260/2.5 |
| 3,984,510 | 10/1976 | Chandra et al. | 264/37 |
| 4,089,206 | 5/1978 | Raffel et al. | 73/19 |
| 4,090,695 | 5/1978 | Stone et al. | 366/76 |
| 4,157,427 | 6/1979 | Ferber | 521/133 |
| 4,299,794 | 11/1981 | Kelley et al. | 422/68 |
| 4,329,869 | 5/1982 | Toda | 73/19 |
| 4,344,710 | 8/1982 | Johnson et al. | 366/76 |
| 4,365,505 | 12/1982 | Hölzl | 73/19.1 |
| 4,376,172 | 3/1983 | Belangee et al. | 521/133 |
| 4,448,902 | 5/1984 | Coblenz et al. | 521/99 |
| 4,470,938 | 9/1984 | Johnson | 264/50 |
| 4,526,907 | 7/1985 | Thiele et al. | 521/133 |
| 4,565,085 | 1/1986 | Grgic et al. | 73/19.1 |
| 4,764,536 | 8/1988 | Proksa et al. | 521/50 |
| 4,862,729 | 9/1989 | Toda et al. | 73/19 |
| 4,906,672 | 3/1990 | Stone et al. | 521/130 |

FOREIGN PATENT DOCUMENTS

| | | | |
|---|---|---|---|
| 0125541 | 4/1984 | European Pat. Off. | |
| 260273 | 5/1970 | U.S.S.R. | 73/38 |
| 1337770 | 9/1987 | U.S.S.R. | 73/866 |

*Primary Examiner*—Hezron E. Williams
*Assistant Examiner*—Joseph W. Roskos

[57] ABSTRACT

Apparatus (10, 180, 260, 270) for incorporating blowing agents into a liquid material provides a high pressure liquid storage and mixing tank (20, 181, 261, 271) containing a mixture of liquid material (M) under pressure; means for delivering (59, 220, 232, 285) a pre-determined quantity of at least one blowing agent into the mixture in minute bubbles or droplets having an average diameter of from about less than 0.2 micron up to about 100 microns; and means for uniformly distributing (60, 110, 237, 276) the blowing agent throughout the liquid material. Apparatus (100, 260, 270) for measuring the volumetric expansion potential of at least one blowing agent and a liquid material component (M) within a closed system comprises a high pressure tank (106, 181, 261) containing liquid material and at least one blowing agent under pressure; means for measuring (135, 240) the volumetric expansion potential of the mixture, providing first (136, 250) and second (138, 251) chambers, communicating with each other and with the tank; means for transferring (142, 143, 243) the mixture into and out of the first and second chambers, the second measuring chamber having a volume sufficiently greater than the volume of the first chamber whereby at least some of the blowing agent will leave the mixture; means for measuring (164, 252) the pressure in the first chamber; and means for measuring (144, 145, 253) the volumes displaced by the mixture within the first and second first chambers. Finally methods are provided for use of the foregoing apparatuses.

43 Claims, 5 Drawing Sheets

5,154,088

APPARATUSES AND METHODS FOR INCORPORATING BLOWING AGENTS INTO LIQUIDS FOR THE PRODUCTION OF POLYMER FOAMS AND FOR MEASURING THE VOLUMETRIC EXPANSION POTENTIAL OF MIXTURES THEREOF

CROSS-REFERENCE TO RELATED APPLICATIONS

This application is a continuation-in-part of U.S. Ser. No. 588,086, filed Jul. 24, 1990 U.S. Pat. No. 5,119,668.

TECHNICAL FIELD

This invention relates to apparatuses and methods to incorporate blowing agents into liquid materials for the manufacture of polymer foams. More particularly, the invention relates to the introduction of blowing agents as minute bubbles or droplets for the purpose of being able to prepare microcellular polymeric products. This invention also relates to an apparatus and method for determining the volumetric expansion potential of a mixture of blowing agent and liquid materials, and means additionally of determining the density and solubility and liquefaction thereof.

BACKGROUND OF THE INVENTION

In the manufacture of polymeric foams, such as, for example, polyurethanes, polyureas, phenol-formaldehydes and the like, a heat activated blowing agent is employed to provide the desired cell structure.

The term liquid material is understood to include any liquid material that can be converted into a polymer by a polymerization reaction. Of particular interest are polyurethane, polyurea and isocyanate polymers which are produced by contacting under reactive conditions suitable amounts of liquid material comprising a polyahl and an isocyanate.

The term polyahl is understood to include any compound containing active hydrogens in the sense of the Zerewitinoff test, see Kohler, Journal of the American Chemical Society, page 381, Volume 49 (1927). Representative active-hydrogen groups include —OH, —COOH, —SH and —NHR where R is H, alkyl, aryl and the like.

The term isocyanate is understood to include organic isocyanates and polymeric derivatives thereof useful in making polyurethanes, polyureas and polyisocyanurates, such as, aromatic, aliphatic and cycloaliphatic polyisocyanates. Exemplary compounds include toluene diisocyanate, diphenylmethane diisocyanate, polymeric diphenylmethane diisocyanate and mixtures thereof.

A crude polyisocyanate may also be used in the practice of this invention, such as, the crude toluene diisocyanate obtained by the phosgenation of a mixture of toluene diamines or the crude diphenylmethane diisocyante obtained by the phosgenation of crude methylene diphenylamine. The preferred undistilled or crude polyisocyanates are disclosed in U.S. Pat. No. 3,215,652, incorporated herein by reference. Derivatives of the above identified isocyanates, such as, prepolymers, are equally suitable for use in the present invention.

This disclosure relates to the manufacture of flexible and rigid foams as well as to systems employed in the manufacturing of reaction injection molded (RIM) and reinforced reaction injection molded (RRIM) products.

Flexible foam processing systems generally utilize polyester or polyether polyahls and toluene diisocyanate (TDI) or diphenylmethane diisocyanate (MDI) and small amounts of catalysts, surfactants and amines. Additionally, various blowing agents are utilized which generally consist of some of the following of methylene chloride and small amounts of R-12 ®, for so-called mechanically blown foams, and water and small amounts of carbon dioxide for so-called chemically blown foam in which water is the primary blowing agent.

Rigid foam processing systems generally utilize polyether polyahls and MDI and small amounts of catalysts, surfactants and amines. Additionally, various blowing agents are utilized which typically consists of a combination of one to two percent of water and approximately 25 to 35 weight percent of chlorofluorocarbon (CFC). The CFC is normally R-11A ®.

RIM and RRIM foam processing systems generally utilize an amine terminated polyol, polyether or polyester polyahls and MDI and TDI and small amounts of catalysts and surfactants. Gaseous nitrogen blowing agent is normally utilized in the form of suspended bubbles or droplets in about a fifty percent by volume concentration at atmospheric pressure conditions. The compressed gas bubbles or droplets present during mold filling aid in complete filling of the mold and enhancement of surface characteristics of the molded product. RRIM differs from RIM, in that reinforcing fillers are added to the above described polyol or polyether polyester polyahls.

In the manufacture of foam products for use as insulation, chlorinated fluorocarbons (CFC's) specifically FREON ® have been employed as the blowing agent because a very small and uniform cell structure results in the product and, in turn, provides an improved K factor. In order to eliminate the use of such CFC's, other blowing agents have been considered. While it has been customary to employ a chlorinated fluorocarbon (CFC) for this purpose, the cumulative effect on the ozone layer of the atmosphere has made it desirable to utilize environmentally friendly blowing agents. Gases including carbon dioxide, nitrogen, helium, ammonia, pentane, acetylene, the inert gases, air and mixtures thereof have been investigated. Unfortunately, the mere addition of some alternative blowing agents is difficult and heretofore has often not resulted in the manufacture of quality foam products.

Introduction of the blowing agent generally gives rise to a number of different types of phase behavior which depend on the miscibility characteristics of the blowing agent/liquid material combination at the given temperature and pressure. Essentially, insoluble blowing agents under high pressure, may give rise to the presence of both droplets of liquid blowing agent and bubbles and gaseous blowing agent in the liquid material, provided the temperature of the system remains below the critical temperature of the blowing agent and the pressure is high enough to cause liquefaction. Under similar conditions, a mixture will contain single, dissolved blowing agent molecules in addition to distinct droplets and bubbles of liquified and gaseous blowing agent, respectively.

In the production of polyurethanes, the blowing agent is mixed with a liquid material or reaction component of a two part system, e.g., polyahl or isocyanate, prior to polymerization. One of the problems associated with the use of non-CFC blowing agents has been their incorporation into the liquid material. For a given cell structure, it is known that a specific quantity of blowing agent must be present, however, the solubility and miscibility of the agent is an important factor with which the manufacturer must reckon.

To date, the patent art provides numerous examples of apparatus and methods for using various non-CFC blowing agents in a variety of liquid material components. For example, the introduction of an inert gas, such as, nitrogen, into a liquid reaction component of a reaction injection molding (RIM) system is taught by U.S. Pat. No. 4,157,427. In general, the gas is added to one of the precursors of a polyurethane by use of a sparger through which the gas is forced, under pressure. The sparger is described as a suitably sized and shaped porous rigid structure, to produce minute bubbles for better mixing, that is placed in a pipe through which the reactive component is circulated from the supply tank and then sent either to a mixing head or back to the supply tank.

U.S. Pat. No. 4,376,172 is directed toward a closed loop apparatus for controlling the addition of a gas to a liquid, such as, polyurethane precursor, in a RIM process. Additionally, means are provided for accurately measuring the amount of the gas that is added. The blowing agent or gas is added by means of a sparger which is in a stream of the reactant being recirculated from the supply tank and back to the supply tank.

Measurement of the amount of gas added to the polyurethane reactant is performed by trapping a volume of the gas-reactant mixture and holding it in a cylinder. A piston is then driven into the cylinder to check, by means of compressibility, the amount of gas which has been added.

U.S. Pat. No. 4,526,907 is directed toward a process and device for charging gas into at least one of the components combined to produce plastic foams. The reactant from one supply tank is piped through a circulation line which has a zone of compression that is higher in pressure than that in the supply tank. In this compression zone the foaming gas is added, and the mixture is subsequently forced through a throttle element to reduce the pressure before return to the supply tank. The patent also teaches that several different methods can be employed to determine the amount of gas in the gas-reactant mixture including density, partial pressure, the absorption of a beam of light, compressibility and solubility, but does not necessarily discuss means for doing so.

U.S. Pat. No. 4,906,672 is directed toward a method for the continuous manufacture of polyurethane foam. More particularly, it deals with the additions of small amounts of carbon dioxide to polyurethane-forming reactants which contain water as the primary blowing agent and teaches that the carbon dioxide is to be dissolved into one of the reactants well before being sent to the mixing head.

Introduction is performed under high pressure, preferably 75 to 900 psig (0.62 to 6.3 MPa), in a pipe, a sufficient distance from the mixing head that uniform entrainment is achieved upon traveling from the sight of impingement to the mixing head. Once the mixture reaches the mixing head, a nozzle or series of nozzles are employed to expand the carbon dioxide-reactant mixture; however, the patent teaches that the entrainment of bubbles is to be avoided. The patent does not contemplate the use of alternative blowing agents or mixtures thereof nor does it contemplate the addition of high concentrations of carbon dioxide as a major blowing agent component.

Finally, European Pat. No. 125,541-B discloses a devices for measuring the gas charging of a liquid component used for producing synthetic plastic foam, such as, a polyurethanes. It employs a measuring vessel, for receipt of a liquid sample periodically, and which communicates with an overflow vessel. By allowing the pressure in the measuring vessel to decrease to atmospheric, the gas laden component expands and overflows to the overflow vessel which allows density to be determined.

The prior art teaches determination of gas loading using measured density of the blowing agent/liquid material mixture at actual operating pressure (U.S. Pat. No. 4,157,427) or at ambient pressure. To this purpose, mixtures of polyahls and blowing agents are expanded either from a preset operating pressure to a second, lower set pressure (U.S. Pat. No. 4,376,172) or from a given preset operating pressure to atmospheric pressure (European Pat. No. 125,541-B). The latter invention utilizes equipment that is large, cumbersome and expensive. Moreover, at least part of the gas in the mixture will be lost from the system during expansion.

Thus, it should be apparent that although others have employed low boiling compounds, as blowing agents for polyurethane foam, apparatus and method have not been taught for the incorporation of a blowing agent into a liquid material, in precise amounts and bubble and droplet sizes so as to control the cell structure of the resulting foam, or for the precise measurement of the volumetric expansion potential of a mixture of blowing agent and liquid material, the liquefaction and solubility of the blowing agent in the mixture, or the determination of it's volumetric expansion potential therefrom. Moreover, previous apparatus and methods have not been successful in providing uniform incorporation of the blowing agent in the liquid material component, which has grossly affected the quality of the resulting foam product.

Another problem has been the accurate determination of the quantity of blowing agent actually incorporated into the liquid material component prior to reaction because escape of the agent during measurement leads to erroneous determinations and, in turn, the use of incorrect quantities of the blowing agent as corrections are made or not made.

Additionally, escape of blowing agents has precluded or made difficult or hazardous the use of flammable blowing agents.

It should also be clear from the above discussion that these methods will provide erroneous results where liquid blowing agent droplets and/or dissolved single blowing agent molecules remain in the liquid material after expansion. In such instances, relatively correct gas loading may be obtained but, the relationship between gas loading and density of the expanded product will be in error to the extent that expansion potential is not accounted for by the density measurement.

SUMMARY OF THE INVENTION

It is therefore an object of the present invention to provide apparatus for the incorporation of soluble and insoluble blowing agents into a liquid material for the production of both rigid and flexible polymer foams.

It is another object of the present invention to provide apparatus for the incorporation of blowing agents into a liquid material for the continuous production of rigid and flexible polymer foams.

It is another object for the present invention to provide methods for the incorporation of soluble and insoluble blowing agents into a liquid material for the production of rigid and flexible polymer foams.

It is yet another object of the present invention to provide a method for the incorporation of blowing agents into a liquid material for the continuous production of rigid and flexible polymer foams.

It is still another object of the present invention to provide apparatus and methods for improved blowing agent loading during the manufacture of polymer foams in RIM and RRIM processes.

It is another object of the present invention to provide apparatus for precisely measuring the volumetric expansion potential of a mixture of a blowing agent and liquid material for the production of rigid and flexible polymer foams.

It is still another object of the present invention to provide methods for precisely measuring the volumetric expansion potential of a mixture of a blowing agent and liquid material for the production of rigid and flexible polymer foams.

It is still another object of the present invention to provide apparatus and methods for control of mass ratio of blowing agent and liquid material in rigid and flexible foams.

At least one or more of the foregoing objects, together with the advantages thereof over known methods and apparatus relating to the use of blowing agents in the production of polymer foam, which shall become apparent from the specification which follows, are accomplished by the invention as hereinafter described and claimed.

In general the present application provides an apparatus for incorporating blowing agents into a liquid material comprising high pressure tank means containing a liquid material under pressure; means for delivering a pre-determined quantity of at least one blowing agent into the liquid material in minute bubbles or droplets having an average diameter of from about less than 0.2 micron up to about 100 microns; and means for uniformly incorporating the blowing agent throughout the liquid material.

Additionally, an apparatus is provided for measuring the volumetric expansion potential of a mixture of at least one blowing agent and a liquid material component within a closed system comprising high pressure tank means containing liquid material and at least one blowing agent under pressure; means for measuring the volumetric expansion potential of the mixture, providing first and second chambers, communicating with each other and with the tank; means for transferring the mixture into and out of the first and second chambers, the second measuring chamber having a volume sufficiently greater than the volume of the first chamber whereby at least some of the blowing agent will leave the mixture; means for measuring the pressure in said first chamber; and means for measuring the volumes displaced by the mixture within the first and second chambers.

The present invention also provides a method for the incorporation of blowing agents into a liquid material comprising the steps of feeding a pre-determined amount of liquid material to a supply tank; supplying a pre-determined amount of at least one blowing agent to the supply tank through means immersed within the liquid material to produce bubbles or droplets having an average diameter of from about less than 0.2 micron up to about 100 microns.

Also provided is a method for measuring the volumetric expansion potential of a mixture of at least one blowing agent and a liquid material within a closed system comprising the steps of withdrawing a quantity of the mixture from a supply tank; feeding the quantity into a first chamber under pressure; allowing expansion of the quantity within the first chamber to a volume sufficiently greater to cause at least some of the blowing agent to leave the mixture.

Finally, the present invention provides an apparatus for incorporating blowing agents into a liquid material and measuring the volumetric expansion potential of a mixture thereof within a closed system comprising high pressure tank means containing a liquid material under pressure; means for delivering a pre-determined quantity of at least one blowing agent into the liquid material in minute bubbles or droplets having an average diameter of from about less than 0.2 micron up to about 100 microns; means for uniformly distributing the blowing agent throughout the liquid material; and means for measuring the volumetric expansion potential of the mixture outside of the tank, providing first and second chambers.

As should become apparent from the following description, the apparatuses and methods for incorporating blowing agents provide a closed system in the sense that a pre-determined amount of blowing agent is delivered directly from a source, to the liquid mixture and then incorporated therein, without escape to the atmosphere. This is of particular importance especially for systems in which flammable blowing agents might be utilized. Understandably, to ensure incorporation of precise amounts of blowing agent, all conduits should be appropriately charged so that the desired blowing agent and amount thereof is actually delivered to the liquid material. In similar fashion, the apparatus and method for measuring the volumetric expansion also provide a closed system inasmuch as samples taken from the mixing vessel are tested without direct contact with the surrounding atmosphere or loss of blowing agent.

Thus it will become evident that the apparatuses and methods are employed to provide a highly effective and accurate system for incorporating minute bubbles or droplets of at least one blowing agent into one or both liquid components of a two component reactive system for the manufacture of polymer foams, as well as for measuring the amount of volumetric expansion potential of a blowing agent/liquid material mixture. The inventions described below are particularly suited for producing polyurethane foams and the use of low boiling blowing agents, but are not necessarily limited thereto. Additionally, the inventions provide a method and means for controlling mass balance of blowing agent and liquid. The apparatuses for incorporating and for measuring can be combined and used in the same overall system or, each can be used separately with other equipment, methods and the like, as well as for the manufacture of other polymer foams.

Usage of the present invention will enable one to expand mixtures of blowing agent and liquid material selectively so as to ensure essentially all blowing agent disengages from the liquid mixture such that expansion potential can be measured. In this way, the correct assessment of final expansion of the potential mixture can be made, irrespective of the properties and composition of the blowing agent/liquid material combination considered. This feature will be unique and highly beneficial to employ new environmentally friendly blowing agent compositions for a plurality of expanded polyurethane products. Optionally, the invention also enables one to expand such mixtures to a desired final pressure, thus allowing for measurement of solubility, density and gas loading as well as the molar or mass ratio of liquid material and blowing agent mixture.

PREFERRED EMBODIMENT FOR CARRYING OUT THE INVENTION

Figure 1:
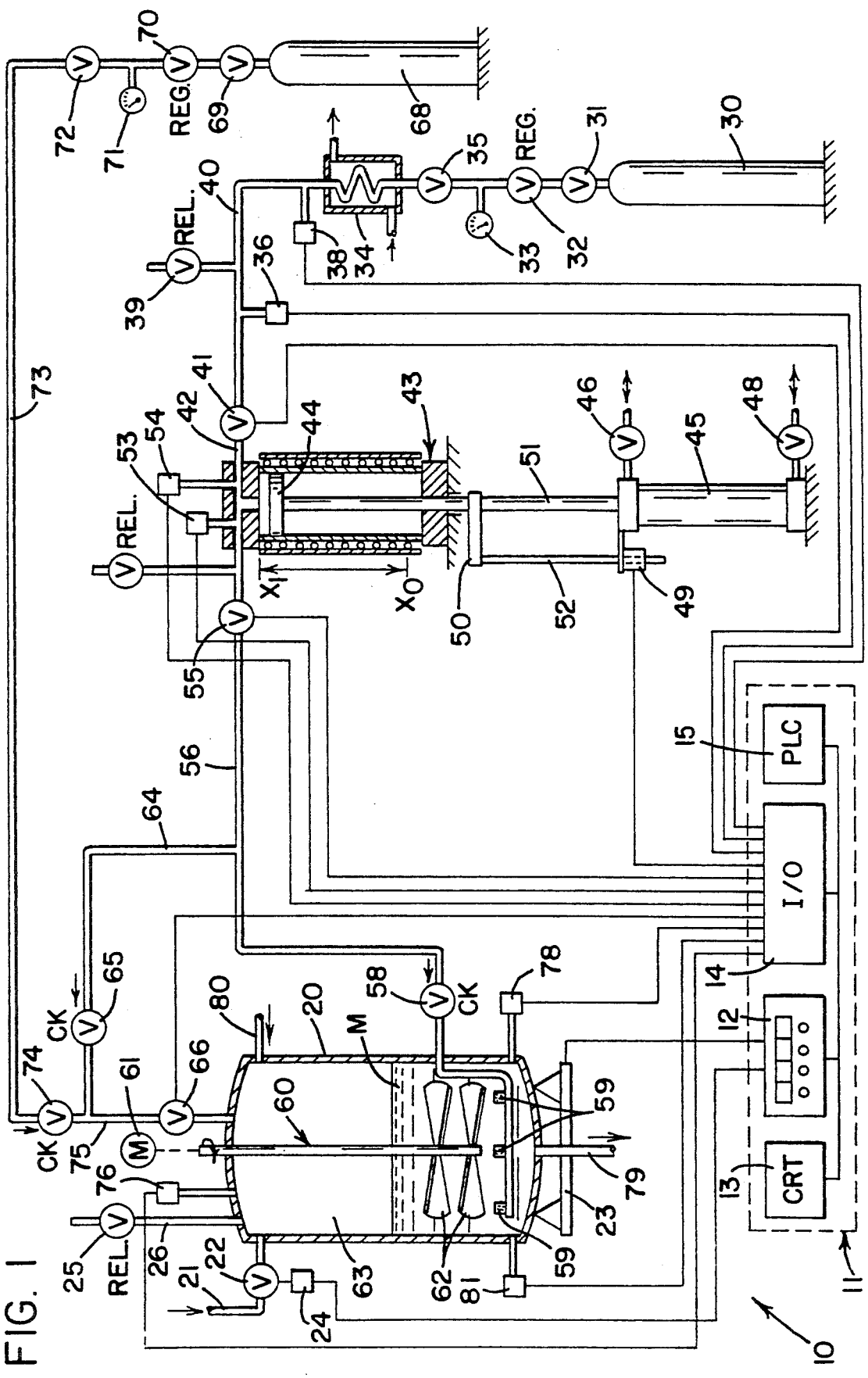
FIG. 1 is a schematic flow diagram of apparatus, according to the present invention, for incorporation of blowing agents into a liquid material employed for the manufacture of polymer foams.

The present invention is related generally to the use of a plurality of blowing agents as the blowing agents for liquid material components of reaction mixtures. In the manufacture of polyurethane foam as a preferred example, two liquid materials, a polyahl component (material M) and a isocyanate component (material N) are prepared separately and then combined in a mixhead. The reaction is quick and the mixture is injected into a suitable vessel or mold or continuous belt or laminator where foaming and expansion occurs and the product is actually formed.

The term blowing agent is understood to include any gases and liquids which are capable of performing in substantially the same manner as the preferred blowing agent described herein for the production of polymer foams, including but not limited to compounds, such as, chlorofluorcarbons (CFC's), hydrochlorofluorocarbons (HCFC), perfluoroalkanes (PFA), hydrofluoroalkanes (HFA's), normal and branched alkanes and mixtures thereof, esters, ethers, noble gases, ammonia, pentane and isomers thereof and mixtures thereof as well as water and steam, carbon dioxide, helium, nitrogen and air as well as any suitable mixture of two or more blowing agents. Nitrogen is especially useful as a blowing agent for the production of polyurethane, RIM and RRIM foams. The present invention accommodates the use of either soluble or insoluble blowing agents, as will become apparent in the description which follows.

The blowing agent or mixture of agents is incorporated into the liquid material forming a mixture thereof. Owing to the different phases and types of mixtures possible, the term "incorporation" as used herein includes mixtures of essentially soluble as well as essentially insoluble blowing agents with liquid material, which are dissolved and distributed or dispersed respectively. Hence, the term mixture can include combinations of an essentially insoluble blowing agent with a liquid material as well as solutions of a soluble blowing agent in a liquid material. It should also be appreciated that liquid and gas blowing agents can be employed and thus, incorporation includes liquid droplets and gas bubbles and molecules. Pressure conditions can also affect liquefaction, as noted hereinabove. In all instances, the present invention provides the uniform incorporation of the blowing agent into the liquid material.

The present invention also describes the addition of a blowing agent to the polyahl component of a polyurethane composition, although it could as readily be employed with the isocyanate component or both. Addition of the blowing agent is precisely controlled to accommodate one or more of the following: incorporation of the proper size bubbles or droplets; precise regulation of the quantity of blowing agent necessary to provide the desired properties of the foam, including density and cell structure and, control over the mass ratio between the liquid material and the blowing agent.

Methods and apparatus for incorporating blowing agents into the liquid mixture, according to the present invention, include means for measuring the quantity of blowing agent to be incorporated and a sparging means to divide the blowing agent into minute bubbles or droplets in the liquid mixture.

Measuring means may include a cylinder and piston wherein temperature, pressure and volume displaced by the piston delivering blowing agent to the liquid mixture are known. Such cylinder arrangement may be used to deliver a wide variety of blowing agents to the liquid mixture wherein the blowing agents may be gaseous or liquid and especially where it is desired to be enabled to choose at will from a variety of blowing agents with different physical characteristics. In the processing of blowing agents, where the physical properties are well-known and the blowing agent has been selected, then various commercially available meters selected for compatibility with the physical properties may be utilized. Such meters may include gear meters, bypass type gas mass flow meters and positive displacement pumps.

Sparging means will be used to divide the blowing agent into minute bubbles or droplets, having an average diameter of up to about 100 microns, preferably about 10 microns, more preferably about 1 micron and most preferably about 0.2 micron.

The method contemplated generally utilizes a pressure capable supply tank for storage of the mixture of blowing agent and liquid material and a pump for circulating the mixture. The sparger means may be located in the tank or in the duct utilized to circulate the mixture or sparger means may be located at both aforementioned locations. A metering means is generally provided from the tank or circulation duct to control precisely the flow of the liquid material mixture to the processing point where the reactive materials are mixed. A sparger means may, alternatively, be provided between the metering means and the processing point.

As will be described hereinafter, the method and related apparatus for measuring the volumetric expansion potential of a mixture of at least one blowing agent and a liquid material employ first chamber and second chambers, within an overall closed system. Because the system is closed, it is no longer necessary to withdraw a quantity of the mixture from the apparatus for evaluation in the open atmosphere which has been inherently inaccurate inasmuch as quantities of the blowing agent escape prior to actual measurement. Moreover, in the open atmosphere, it is generally not possible to draw off all of the blowing agent and hence, further inaccuracies result. Upon expansion of the mixture from the first chamber to the second, at least some of the blowing agent will leave, and by determining such amounts, it is possible to adjust and control the amount of blowing agent actually incorporated in the liquid component which, in turn, provides a greater control over the production of foam products than heretofore possible and, a better product.

The volume of the second chamber can be as great as three orders of magnitude or greater then the volume of the first chamber in processes where the blowing agent loading is relatively high, such as, will be the case for flexible and rigid foam processes. The volume of the second chamber, for processes, such as, RIM and RRIM where the blowing agent loading is relatively low and especially when the blowing agent is essentially insoluble, may be much less than one order of magnitude greater than the first chamber and may, in fact, be less than the volume of the first chamber but is preferred to be between one and two times greater.

The mixture of liquid material and blowing agent is preferred to be continuously flowing through measuring apparatus at all times that a measurement is not being made. Flow can be initiated and/or maintained by appropriate devices arranged to induce flow through the measuring apparatus.

The apparatus for measuring volumetric expansion may be installed as a parallel side stream to a primary flow conduit. The pressure difference necessary to induce flow through the apparatus will be caused by the well known fluid dynamic frictional pressure losses inherent in viscous fluid flow.

In the preferred embodiment of the measuring apparatus, the first chamber may be the volume defined by the cavity between two valves. Additionally, there may be a cylinder and piston arranged to communicate with the cavity between the valves so that the volume of the first chamber may be varied. The second chamber is preferred to be a cylinder and piston arranged to communicate with the cavity between the valves. The volume of the cavity will be known. The cross sectional area of cylinders and pistons utilized will also be known. Controlling and knowing the stroke of the pistons will be used to calculate the volumetric expansion of any mixture of liquid material trapped between the valves. Such trapped mixture of liquid material and blowing agent will be referred to as a "sample". The functioning of the apparatus will be as follows: the first chamber piston, if used, will increase the first chamber volume to a predetermined size; the valves will close, thus trapping a sample; the second chamber will be moved in order that the volume occupied by the sample is increased. Temperature of the sample may be controlled as necessary to assist in causing the blowing agent to separate from the mixture. Pressure temperature and volume of the expanding mixture will be recorded and logged by conventional microprocessor equipment.

Expansion of the sample may be to any ratio of second to first chamber volume deemed proper for the mixture of liquid material and blowing agent. In the case of flexible foam and rigid foam processes where highly soluble or liquified blowing agents may be used, it may be necessary to expand the mixture to below atmospheric pressure i.e., partial vacuum in order to cause the blowing agent to separate from the mixture to the extent necessary to obtain an accurate measurement. This is to be understood to mean that liquified and/or dissolved blowing agents are driven from the liquid in a gaseous state to the extent that measurement of the quantity of these blowing agents can be accurately determined.

The pressure, volume and temperature data, thus logged during expansion of the sample, will be used with the well-known gas laws to determine the molar quantity of blowing agent present. From this data may be calculated the expansion potential of the mixture from one processing condition of pressure and temperature to another as occurs during the mold filling part production, or other processing.

Optionally, the volumetric expansion potential of the mixture under pressure in the supply tank may be determined by expanding the volume of the second chamber to any desired lesser extent than is required to separate essentially all blowing agent from the mixture.

In the case of the RIM and RRIM process where essentially insoluble blowing agents are utilized, the expansion potential and mass ratio of blowing agent and liquid material can be determined directly given any expanded volume and corresponding pressure; however, for this process it will be desirable to expand to 0.0 gauge as this provides a closed loop improvement of open cup methods practiced today. Improvements consist of automation, waste reduction, elimination of chemical exposure to the operator, elimination of cleaning of the equipment, and elimination of inherent errors due to variations in technique of the operators.

Additionally, liquefaction of blowing agents within the mixture, and the solubility of various blowing agents in liquid materials, density and specific gravity of the mixture at any expansion ratio may be determined for any mixture of blowing agents and liquid material.

It should be apparent to those skilled in the art that the aforementioned methods and apparatuses for incorporating blowing agents into liquids and for measuring the expansion potential of mixtures of liquid materials and blowing agents coupled with easily gathered data regarding the quantity of liquid raw material being consumed that an accurate mass balance may be known.

This, for the first time, makes available a number of novel control features. For the processes which will use essentially insoluble blowing agents, such as, is done in RIM and RRIM, it will be made possible to detect trends of operating conditions which can predict when unsatisfactory parts will be made. Since the blowing agent contemplated is essentially insoluble in the liquid material and, therefore, exists in the liquid as discrete gas bubbles, it is well-known that some of the bubbles will be coalescing. There will, therefore, be a positive flow of coalesced gas bubbles too large to remain dispersed in the liquid mixture from the surface of the liquid mixture. The rate of positive gas flow can only be modified but not prevented so a vent must be provided in order that the desired pressure regulation can be maintained for the process and so that the blowing agent lost from the liquid mixture may be replaced. The quantity of gas lost through the vent will be measured.

Since the total mass flow of blowing agent introduced to the liquid is known and the molar ratio of blowing agent dispersed within the liquid mixture is known and the rate of consumption of the mixture of liquid material and blowing agent is known and finally that the mass flow rate of gas lost from the vent is known, then it can be deduced that:

1- The present operating conditions are within the set-point limits of historical operating guidelines.
2- The rate of blowing agent addition and vented gas are both abnormally high, therefore, the coalescence rate is abnormally high. This means that the liquid material is having difficulty retaining the blowing agent and that mold filling or other processing will likely result in unacceptable product. The operator can be forewarned of such deterioration in proper operating conditions prior to manufacturing scrap product so that steps can be taken to correct the conditions responsible.
3- The rate of blowing agent addition is abnormally high but the rate of vented gas is normal. This will indicate a leak in the system. In such systems leaks most often develop at the rotating shaft seal of the agitator of the pressurized storage vessel for the mixture of liquid material and blowing agent. Deterioration of the seal can, thus, be detected and maintenance arranged in order that unscheduled loss of production capability is avoided.

Other incongruities in setpoints can point to faults in one or more of the measuring or loading systems.

It will also be apparent to those skilled in the art that knowledge and control of the mass balance will enable these processes to be operated more closely to steady state by utilizing for the first time a control concept known as "feed forward". This will be useful in flexible and rigid foam processes but it will be of particular benefit to RIM and RRIM processes.

Since the RIM and RRIM processs utilizes an essentially insoluble blowing agent, the presence of the blowing agent present in discrete bubbles will significantly reduce the density of the mixture of liquid material and blowing agent. As the mixture is consumed, it must be replaced. The addition of this liquid material without blowing agent may be anticipated by the control programmable device normally utilized so that as the added liquid material passes the sparger, the flow rate of blowing agent will be appropriately increased in order to correct the mass ratio. The correction is anticipated, calculated and completed before the added liquid material reaches the expansion potential measuring device (feed forward control) and, thus, deterioration from operating set point conditions is avoided.

With respect now to the drawings, apparatus, indicted generally by the numeral 10, is depicted in FIG. 1. Apparatus 10 includes approximately one-half of a two component liquid material system, e.g., polyahl and polyisocyanate, for the manufacture of polyurethane. For purposes of discussion, apparatus 10 shall be described in conjunction with the polyahl liquid material component.

Apparatus 10 provides an operator panel 11, housing a digital indictor module 12, a video display monitor (CRT) 13, an input/output control panel 14 and a programmable logic controller (PLC) 15. As is known in the art, the operator panel is connected to a plurality of valves and transducers for operation of the component elements of apparatus 10 which shall be described next.

A liquid material holding and mixing tank 20 is provided for receipt of a supply of material M. Tank 20 is designed to withstand pressures of up to about 1000 psig (7.0 MPa) and is fed via conduit 21, through valve 22 a supply of liquid material from a source (not shown). Preferably the pressure within the material tank may be about 600 psig (4.1 MPa) and most preferably about 435 psig (3.0 MPa). Nevertheless, it is to be understood that even higher pressures are not to be precluded, if a desired material and blowing agent combination may eventually require such pressure, and similarly, pressure as low as 0 psig (0.1 MPa) may be suitable with other combinations.

Tank 20 is positioned over a load cell 23 so that a pre-determined amount of material M selected by the digital indicator module 12 is delivered. Upon reaching the pre-determined weight, a signal from the module 12 will energize the solenoid 24 to close valve 22. A relief valve 25 is provided to vent gas via conduit 26 while the tank 20 is filled. The weight of liquid material M is now read from indicator module 12.

A supply tank 30 is provided for the delivery of blowing agent via exit valve 31, pressure regulator 32, pressure gauge 33, and heater 34, controlled by valve 35. Temperature and pressure of the blowing agent are measured by transducers 36, 38 and indicated on the CRT 13, with excess pressure being relieved through valve 39 in conduit 40.

Blowing agent is fed through control valve 41 and conduit 42 into a delivery cylinder 43 which contains a piston 44. Piston 44 is, in turn, driven by hydraulic cylinder 45, located in tandem with cylinder 43. Speed and movement thereof are controlled by valves 46 and 48. Because the area of the piston 44 and cylinder 43 are constant, it is only necessary to establish the distance of piston travel between points $X_0$ and $X_1$ to establish a pre-determined quantity of blowing agent.

Based upon the percent of blowing agent required to reduce the expanded product, typically ranging from about two to thirty percent by weight, the quantity of the blowing agent to be fed into cylinder 43 is calculated and the set points $X_0$ and $X_1$ are displayed on the CRT 13.

A position transducer 49 is employed to provide electronic feedback as to the position of piston 44. As depicted in the drawing, an arm 50 is carried by the piston rod 51 from cylinder 45 which, in turn, positions a linear position transducer rod 52 for precisely determining the location of piston 44. When the piston 44 is at position $X_1$, a signal is given to stop the stroke.

The inlet valve 41 is opened and the piston 44 is retracted to the position $X_0$, filling the cylinder 43 with the correct quantity of blowing agent until pressure and temperature transducers 53 and 54, respectively, indicate the correct operating parameters, from about 0 psig (0.1 MPa) to about 1000 psig (7.0 MPa) with about 435 psig (3.0 MPa) being preferred and a temperature of from about 60° to 180° F. (16° to 86° C.), with about 110° F. (44° C.) being preferred.

The piston 44 is now urged from position $X_0$ to $X_1$ to deliver the blowing agent through exit valve 55 and conduit 56, over check valve 58 and through a series of spargers 59 located near the bottom of tank 20. The spargers are of a porosity to create minute gas bubbles or droplets having an average diameter of up to about 100 microns, preferably about 10 microns, more preferably about 1 micron and most preferably about 0.2 micron. Orientation of the spargers 59 is horizontal, rather than vertical, to cover a large area of the tank 20.

After introduction of the blowing agent, it is important that the liquid material be mixed thoroughly to keep the blowing agent uniformly incorporated. An agitator 60 driven by motor 61 provides suitable mixing blades 62 to maintain distribution of the blowing agent. At this stage, the combined weight of the material and blowing agent can be checked and if additional amounts are necessary, the foregoing sequence of steps may be repeated.

Because one element of the process is high pressure introduction of blowing agent, it may be necessary to fill the vapor space 63 above the material in tank 20 with a pressurized gas, blowing agent may be utilized if it is a suitable gas. This can be accomplished by directing the gas from tank 30 through conduit 64, check valve 65 and inlet valve 66. If a different gas is desired as a blanketing gas, it can be fed from a source 68 through exit valve 69, regulator 70, pressure gauge 71, control valve 72, conduit 73 and check valve 74 into conduit 75.

The correct blanket pressure is indicated by pressure transducer 76 and once the total liquid and blanket pressure have ben indicated from a signal of the presure transducer 78, the polyahl is now circulated out conduit 79 by a pump (not shown) and through a heat exchanger (not shown) and returned to the tank via conduit 80. The operating temperature is indicated from a signal of temperature transducer 81.

When both polyahl and isocyanate are ready for reaction, material M (polyahl) is directed out of the tank via conduit 79 for reaction with the polyisocyanate in a mixhead (not shown).

Figure 2:
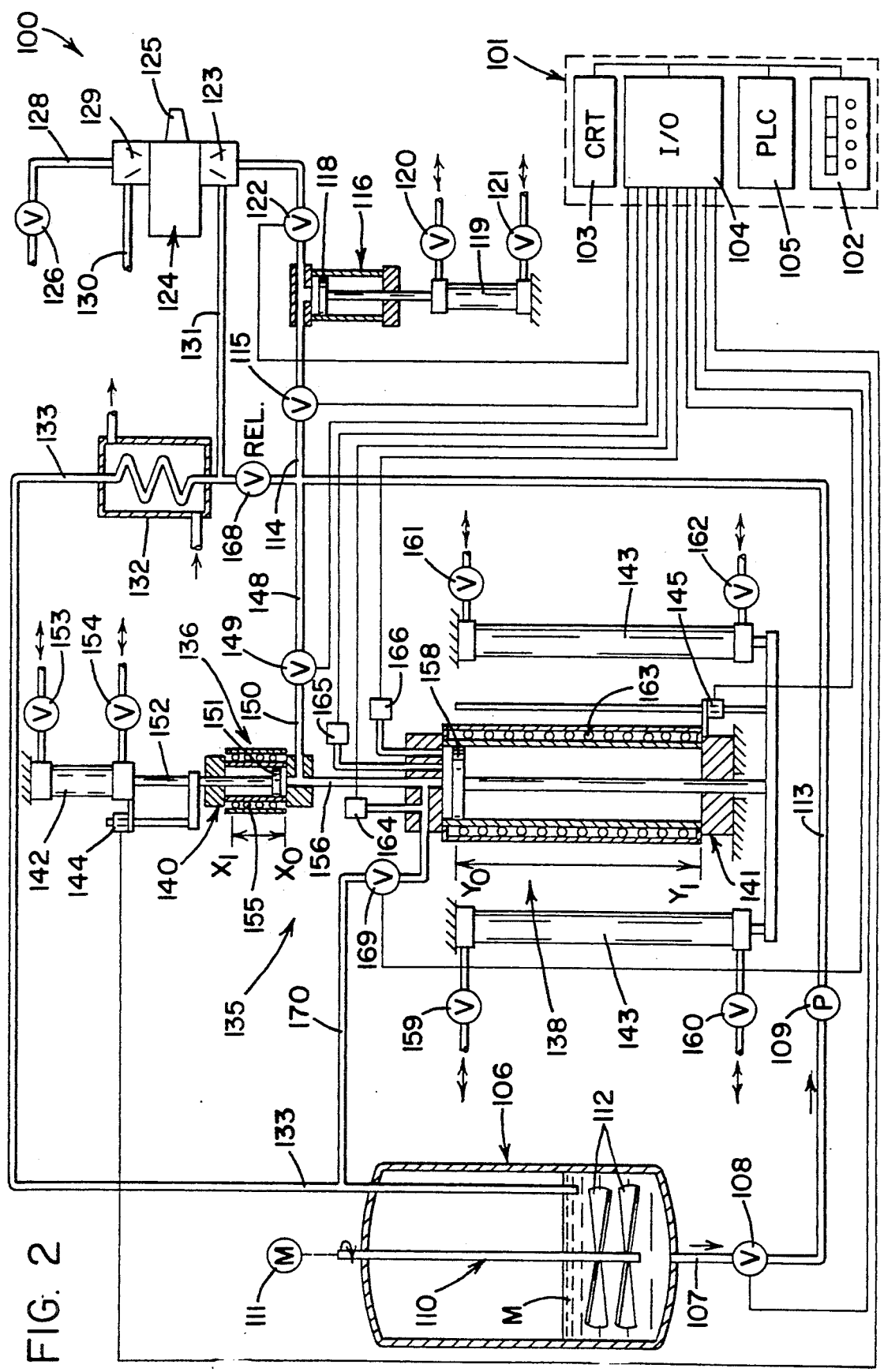
FIG. 2 is a schematic flow diagram of apparatus, according to the present invention, for measuring expansion potential and optionally density, liquefaction and solubility of a blowing agent in a liquid material mixture employed for the production of polymer foams.

With reference to FIG. 2, an apparatus for determing the volumetric expansion potential of a stream of liquid material and blowing agent and indicated generally by the numeral 100, shall be described next. For simplicity again, only one of the two material streams has been depicted.

Apparatus 100 includes an operator panel 101 which houses a digital indicator module 102, a CRT 103, input/output control panel 104 and PLC 105. It provides a liquid material tank 106, similar to tank 20 in FIG. 1, which is designed for pressures up to about 1000 psig (7.0 MPa). Tank 106 contains a quantity of liquid material M, from a source (not shown) and is also supplied with a blowing agent.

Again, in the interest of simplicity, the related structure for introduction of the blowing agent, such as depicted in FIG. 1, has not been shown although it is to be understood that the present apparatus for the measurement of volumetric expansion potential can be employed in conjunction with the apparatus 10, or it can be employed with other blowing agent/liquid material mixtures produced as known in the art.

The liquid material is withdrawn from a conduit 107 at the base of the tank 106, through a valve 108 and pump 109 for reaction with the second component or, for measurement of the volumetric expansion potential. The tank contents are mixed by agitator 110 driven by motor 111 and providing blades 112 to maintain uniform incorporation of the blowing agent.

For purposes of reaction, the material is fed via conduits 113 and 114, through inlet valve 115 to the metering cylinder 116, under a pressure of between about 0.0 psig (0.1 MPa) and 1000 psig (7.0 MPa), preferably 435 psig (3.0 MPa), as discussed hereinabove. Cylinder 116 provides a piston 118, actuated by a hydraulic cylinder 119, equipped with hydraulic control valves 120, 121. The material M is drawn into cylinder 116, then valve 115 is closed and valve 122 is opened and the material is charged through a convergent nozzle 123 in a mixing head 124 and finally through exit chamber 125. The second reactive material, such as, a polyisocyanate, will be simultaneously injected through valve 126 and conduit 128, convergent nozzle 129 in mixing head 124 and through exit chamber 125, thoroughly mixed with the material M (polyahl). When the mixing head is closed, both streams will be returned to their respective tanks via conduits 130 and 131. The stream flows through heat exchanger 132 and is returned via conduit 133 to the tank 106.

For measuring the volumetric expansion potential of the stream, a means for measuring is employed, indicted generally by the numeral 135. Means for measuring comprises first and second measuring chambers or cylinders, 140 and 141 respectively, first and second means for the movement of blowing agent/liquid material mixture into and out of the first and second cylinders, 142 and 143 respectively, and first and second means for measuring the volumes displaced by the first and second cylinders during use, 144 and 145 respectively. A quantity of blowing agent/material is fed from tank 106 through conduit 148, valve 149 and conduit 150 and into first cylinder 140. Cylinder 140 contains a piston 151 and a piston rod 152 driven by a hydraulic cylinder, or first means for movement 142, operated by hydraulic control valves 153, 154. Means for measuring 144 comprises a linear position transducer which is connected to the input/output control panel 104 to withdraw a precise volume of blowing agent/material mixture. The volume of the mixture is controlled. The temperature is controlled by heating element 155 which encompasses cylinder 140. Volume, temperature and pressure are the same as stated hereinabove and need not be repeated here.

The second cylinder 141 provides for mixture expansion control and measuring and is appropriately sized to provide a volume increase of at least one order of magnitude e.g., from about ten times the volume of cylinder 140, and upward to three orders of magnitude or higher. This will result in a pressure drop from a high of about 1000 psig (7.0 MPa) to atmospheric or less than atmospheric pressures, i.e., a partial vacuum.

The mixture is driven from cylinder 140 via conduit 156, into the cylinder 141 as the piston 158 is withdrawn via second means for movement 143, driven by hydraulic control valves 159-162. Cylinder 141 is also provided with heating means 163 and, the second means for measuring 145 comprises another linear position transducer. Pressure transducers 164, 165 and temperature transducer 166 are also provided and are connected to the input/output control panel 104.

For measurement of volumetric expansion potential, the valve 115 is closed and pump 109 circulates the mixture over back pressure relief valve 168, heat exchanger 132 and conduit 133 to the tank 106, in order to provide precise temperature conditioning of the mixture. Once all of the pre-determined conditions have been met, return valve 169 is closed and both cylinders 140 and 141 are in the closed positions $X_0$ and $Y_0$ respectively. The piston 151 of first cylinder 140 is now moved at a controlled rate by means 142 to the $X_1$ position based upon information supplied by the PLC 105. Inasmuch as the area of the piston is constant, it is only necessary to input the distance travelled in order to obtain the volume of the mixture. A comparator in the PLC 105 is provided to compare the actual distance travelled through a signal from the transducer 144. Pressure and temperature from transducers 164, 165 and 166 are also checked and compared.

Valve 149 is moved to the closed position and then the piston 151 of cylinder 140 is moved toward the $X_0$ position while at the same time, the piston 158 of the second, or expansion cylinder 141, is moved by means of 143 toward a position such that a volume of the mixture is transferred from the first to the second cylinder.

Alternatively, the piston 151 may be allowed to remain in the $X_1$ position or it may be moved to any alternate position within cylinder 140, in order that the total volume of the first and second chambers available for the following expansion step may be modified. The modification of volume will be accomplished with greater precision than is described by the following step by approximately the ratio of volumes of the second to the first chambers. This will be useful in determining precise solubility and liquefaction characteristics for particular blowing agents.

In the second step, the piston 158 is moved to a position such that the pressure can be reduced to cause essentially all the blowing agent to separate from the mixture. Because the volume of the second cylinder 141 is greater by at least one order of magnitude than that of the first cylinder 140, the blowing agent will separate from the mixture.

When the piston 158 of cylinder 141 has moved toward the $Y_1$ position to the extent that pressure transducer 165 reads the pressure set to such a level necessary to cause essentially all blowing agent to separate from the mixture, the distance travelled will be provided through a signal from the linear position transducer 145. Upon completion of the measurement, the piston 158 of the expansion cylinder 141 will move toward the $Y_0$ position. If piston 151 is not already at the $X_0$ position it will, at this time, be moved to that position. Opening valve 169 and valve 149 will permit all residue to be purged over conduit 170 to the tank 106.

It will be noted that the first chamber 136 includes all of the volume within the cylinder 140, with piston 151 retracted to position $X_1$; the volume within conduit 150 between valves 149 and 169 when closed; and the volume within the top of cylinder 141, with piston 158 extended to position $Y_0$. The second measuring chamber 138 includes the volume of the first chamber 136 and additionally, all of the increased volume within the second cylinder 141 upon movement of piston 158 to position $Y_1$.

Thus, several opportunities are presented for measuring the volumetric expansion potential of the mixture. First, as described in detail hereinabove, both pistons can be moved to transfer the quantity of mixture from cylinder 140 to cylinder 141. Second, with piston 151 stationary in position $X_0$, and valves 149, 169 closed, piston 158 can be withdrawn from cylinder 141. Third, with piston 158 stationary in position $Y_0$, and valves 149, 169 closed, piston 151 can be withdrawn from cylinder 140. For some measurements it may not be necessary to expand the mixture fully e.g., from cylinder 140 to cylinder 141 and thus, accurate and satisfactory data can be obtained via the foregoing alternatives.

Thus, the apparatuses and methods of the present invention can be employed to allow at least some of the blowing agent to leave the mixture of liquid material and blowing agent and, in some instances, to allow essentially all of the blowing agent to leave the mixture.

As noted hereinabove, the present invention also provides apparatus and methods for improved control during the manufacture of polymer foams in RIM and RRIM processes. To do so, the blowing agent is generally insoluble in the liquid mixture and it is important to be able to control incorporation thereof as well as the precise measurement of the volumetric expansion potential of the liquid and blowing agent. Generally, the greater volumetric expansion potential of apparatus 100 and means for measuring 135 is useful with soluble blowing agents. For insoluble blowing agents, a lesser volumetric expansion potential can be employed, as will be described hereinbelow in conjunction with FIGS. 3 and 4. Whereas, apparatus 10 of FIG. 1 employed a delivery cylinder 43, the apparatus about to be described dispenses with this element. Apparatus 10 is useful for the delivery of a predetermined mass of any one or more different gases to the liquid, but where a specific gas will be employed, a simpler apparatus can be employed.

Figure 3:
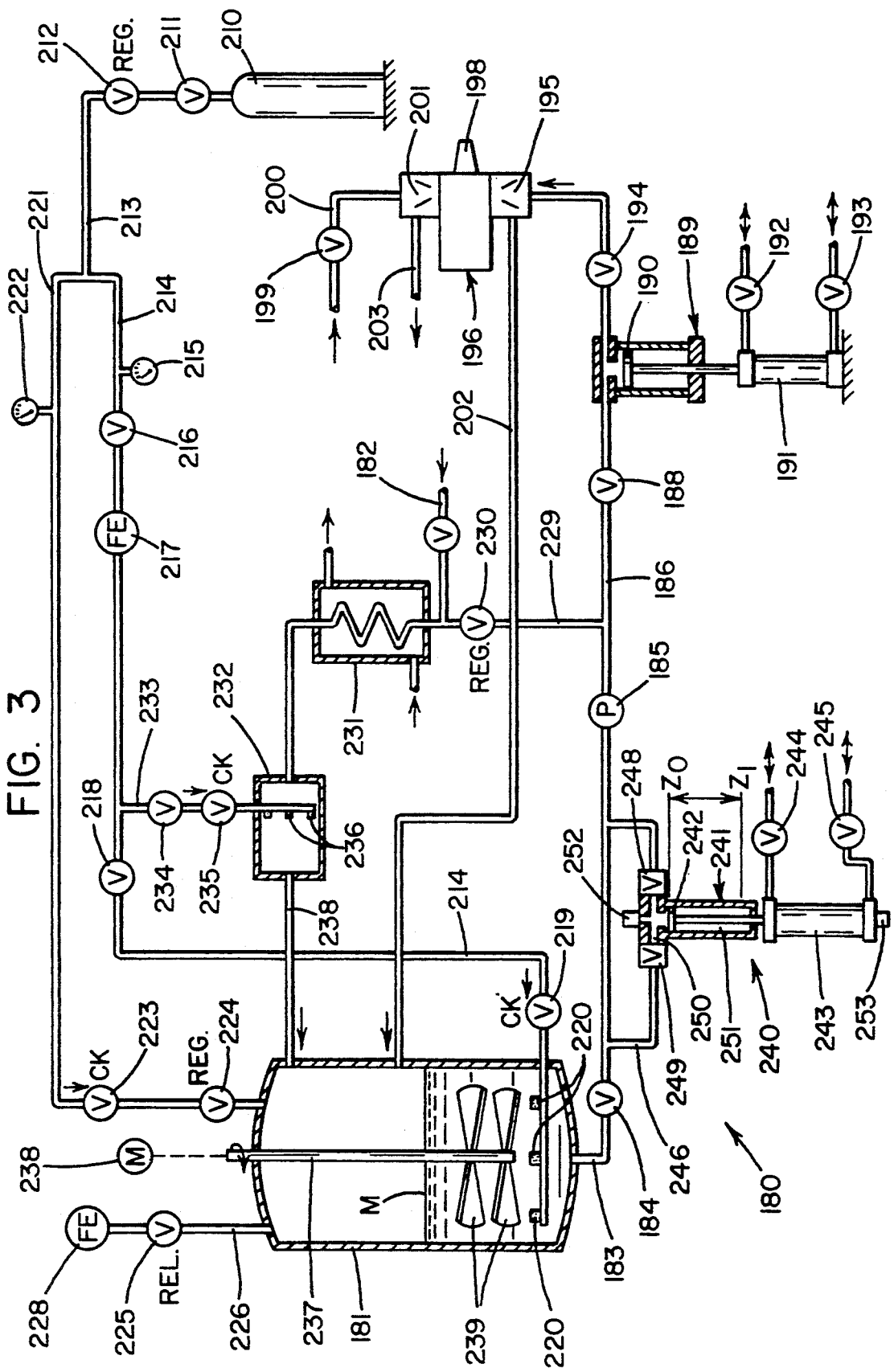
FIG. 3 is a schematic flow diagram of apparatus, according to the present invention, for incorporation of blowing agents into a liquid material employed for the manufacture of polymer foams as utilized by a typical RIM or RRIM process.

With reference to FIG. 3, the apparatus is indicated generally by the numeral 180. Apparatus 180 utilizes an appropriate digital control system, as described in conjunction with FIGS. 1 and 2 hereinabove. However, inasmuch as such systems are well known and do not constitute novelty herein, no further description is deemed necessary. Apparatus 180, as depicted, includes approximately one-half of a two component liquid material system, e.g., polyahl and isocyanate, for the manufacture of polyurethane. For purposes of discussion, apparatus 180 shall be described in conjunction with the polyahl liquid material component.

A liquid material holding and mixing tank 181 is provided for receipt of a supply of material M. Tank 181 is designed to withstand pressures of up to about 500 psig (3.5 MPa) and is fed via conduit 182, a supply of liquid material from a source (not shown). Preferably, the pressure within the tank 181 may be about 250 psig (1.8 MPa) and most preferably about 100 psig (0.79 MPa). Nevertheless, it is to be understood that even higher pressures are not to be precluded, if a desired material and blowing agent combination may require such pressure, and similarly, pressures as low as 40 psig (0.37 MPa) may be suitable with other combinations.

Liquid material is withdrawn from a conduit 183 at the base of the tank 181, through a valve 184 and pump 185 for temperature conditioning, addition of blowing agent and for reaction with the second component or, for measurement of the volumetric expansion potential. For purposes of reaction, the material is fed via conduit 186 and inlet valve 188 to the metering cylinder 189, which is essentially the same as metering cylinder 116 of FIG. 2, under a pressure of between about 150 psig (1.1 MPa) and 600 psig (4.2 MPa), preferably 400 psig (2.9 MPa). Cylinder 189 provides a piston 190, actuated by hydraulic cylinder 191, equipped with hydraulic control valves 192, 193. The material M is drawn into cylinder 189, then valve 188 is closed and the material is passed through valve 194 and is charged through a convergent nozzle 195 in a mixing head 196 and finally through exit chamber 198. Charging pressures range from about 1100 psig (7.7 MPa) and 3000 psig (20.8

MPa), preferably 2800 psig (19.4 MPa). The second reactive material, such as a polyisocyanate, will be simultaneously injected through valve 199 and conduit 200, convergent nozzle 201 in mixing head 196 and through exit chamber 198, thoroughly mixed with the material M (polyahl). When the mixing head is closed, both streams will be returned to their respective tanks via conduits 202 and 203.

As note hereinabove, this apparatus is intended to employ an essentially insoluble blowing agent, hence supply tank 210 is provided for the delivery of blowing agent via exit valve 211 and pressure regulator 212, into line 213. Line 213 is bifurcated, providing a line 214, which carries a pressure gauge 215, valve 216, mass flow meter 217, valve 218, check valve 219 and through a series of spargers 220, positioned within the bottom of tank 181. The spargers are of a porosity to create minute gas bubbles or droplets having an average diameter of up to about 100 microns, preferably about 10 microns, more preferably about 1 micron and most preferably about 0.2 micron. Orientation of the spargers 220 is horizontal, rather than vertical, to cover a large area of the tank 181. A second line 221, carries a pressure gauge 222, check valve 223 and regulating valve 224 and feeds into the top of tank 181, providing a blanket of blowing agent over the liquid. Excess pressure in the tank is relieved through regulating valve 225 in conduit 226 and is measured by a second mass flow meter 228. Regulating valve 224 will be set to operate at a pressure significantly below the setting of the regulating valve 225 so that normally there is no flow through conduit 221.

During circulation of the liquid in line 183, a portion can be returned to the tank 181 without passing through the mixhead 196. Liquid is diverted through line 229 and pressure regulating valve 230 through a heat exchanger 231. Upon leaving the heat exchanger, the liquid is fed through a separate sparger unit 232, which is fed blowing agent by line 233, diverted from line 214. A valve 234 and check valve 235 are employed and the blowing agent is released through spargers 236 which are the same or similar to spargers 220 in the tank. Out of the sparger unit 232, a line 238 carries the liquid material mixture back into the tank 181. Additional, or fresh liquid material, via line 182, is also fed through heat exchanger 231 and sparger unit 232, so as not to dilute the liquid material/blowing agent mixture in tank 181, or the temperature thereof. Contents of the tank are mixed in a conventional fashion by an agitator 237, driven by motor 238 and having suitable mixing blades 239.

When it is desired or necessary to measure the volumetric expansion potential of the mixture, the apparatus provides means for measuring, indicated generally by the numeral 240 which is an alternative embodiment to the first and second chambers as described hereinabove. Means for measuring 240 comprises an expansion cylinder 241, having a piston 242, movable by a cylinder 243 equipped with valves 244 and 245. A portion of the liquid is diverted from line 183 in a parallel side stream line 246. In actuality, a first chamber 250 is defined by the volume between valves 248 and 249 and the top of the piston 242, when the piston 242 is fully extended, as indicated by position $Z_0$. A second chamber 251 is provided by the total fixed volume of the first chamber 250 added to the volume created by withdrawing piston 242 in expansion cylinder 241 as indicated by position $Z_1$.

Pressure of the mixture is captured by transducer 252 and then piston 242 is withdrawn until the pressure within the chamber has fallen to the desired reduced pressure. At this point, the length of travel of piston 242 is captured by transducer 253 and the expansion potential of the mixture is measured. After sampling is complete, the piston 242 is moved to the $Z_0$ position to recompress the sample; valves 249 and 248 are opened to allow the sample chamber to be purged.

Figure 4:
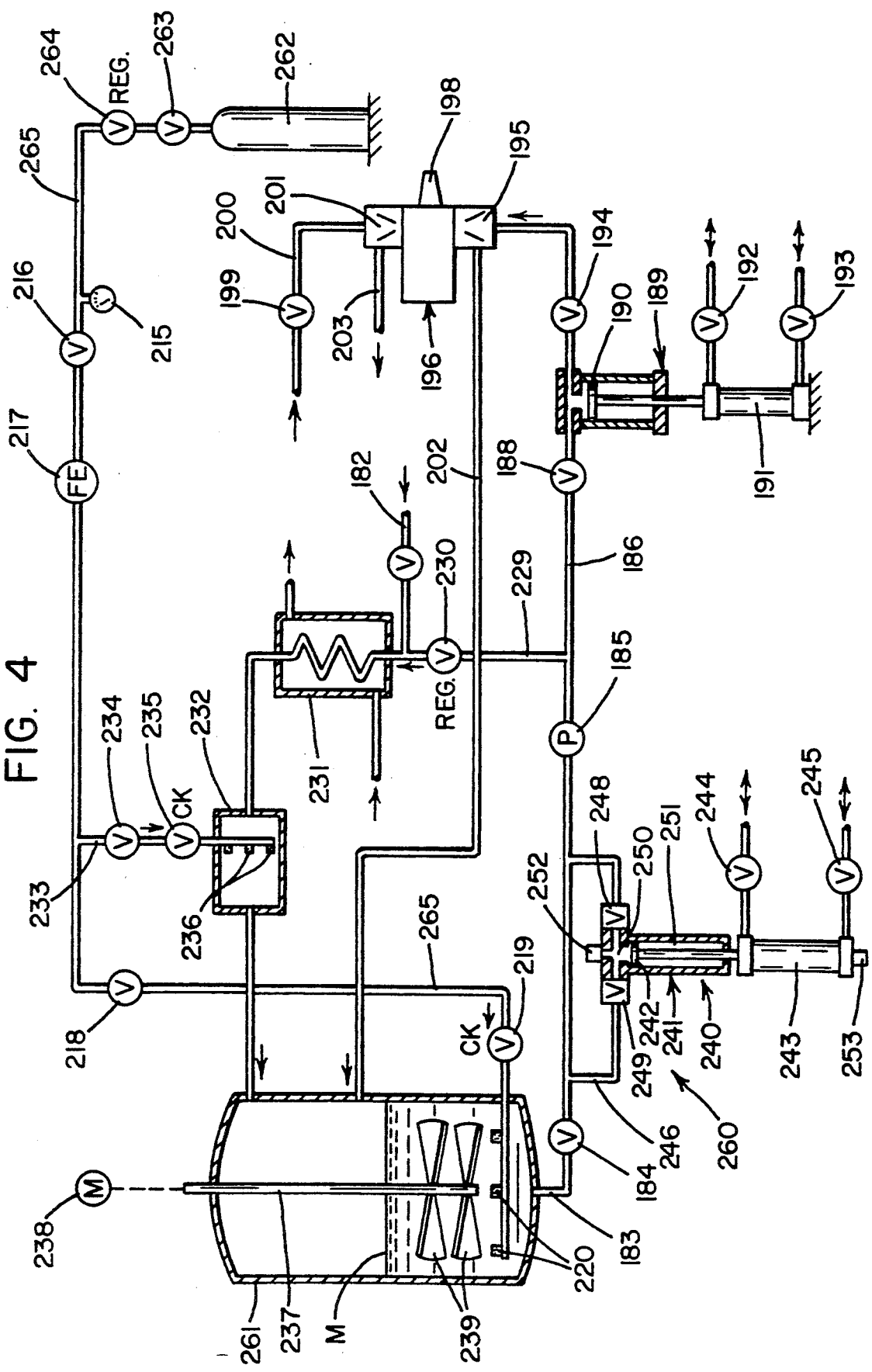
FIG. 4 is a schematic flow diagram of apparatus, according to the present invention, for incorporation of blowing agents into a liquid material employed for the batch production of polymer foams as typically utilized for flexible and rigid foams.

FIG. 4 illustrates another embodiment for the incorporation of a blowing agent, into a liquid material and for precise measurement of the volumetric expansion potential of the liquid and blowing agent which incorporates several essential features of the invention.

With reference to FIG. 4, suitable apparatus is indicated generally by the numeral 260. The apparatus 260 is somewhat similar to the apparatus 180 of FIG. 3 as will become apparent from the description which follows. Accordingly, like components have been designated with the same numbers where appropriate. Apparatus 260 utilizes an appropriate digital control system, as described in conjunction with FIGS. 1 and 2 hereinabove. However, inasmuch as such systems are well known and do not constitute novelty herein, no further description is deemed necessary. Apparatus 260, as depicted, includes approximately one-half of a two component liquid material system, e.g., polyahl and isocyante, for the manufacture of polyurethane. For purposes of discussion, apparatus 260 shall be described in conjunction with the polyahl liquid material component.

A liquid material holding and mixing tank 261 is provided for receipt of a supply of material M. Tank 261 is designed to withstand pressure of up to about 1000 psig (7.0 MPa) and is fed via conduit 182, a supply of liquid material from a source (not shown). Preferably, the pressure within the tank 261 may be about 600 psig (4.1 MPa) and most preferably about 435 psig (3.0 MPa). Nevertheless, it is to be understood that even higher pressures are not to be precluded, if a desired material and blowing agent combination may require such pressure, and similarly, pressures as low as 0 psig (0.1 MPa) may be suitable with other combinations.

Liquid material is withdrawn from a conduit 183 at the base of the tank 261, through valve 184 and pump 185 for temperature conditioning, addition of blowing agents and for reaction with the second component or, for measurement of the volumetric expansion potential. For purposes of reaction, the material is fed via conduit 186 and inlet valve 188 to the metering cylinder 189, which is essentially the same as metering cylinder 116 of FIG. 2, under a pressure of between about 150 psig (1.1 MPa) and 600 psig (4.2 MPa), preferably 400 psig (2.9 MPa). Cylinder 189 provides a piston 190, actuated by hydraulic cylinder 191, equipped with hydraulic control valves 192, 193. The material M is drawn into cylinder 189, then valve 188 is closed and the material is passed through valve 194 and is charged through a convergent nozzle 195 in a mixing head 196 and finally through exit chamber 198. Charging pressures range from about 1100 psig (7.7 MPa) and 3000 psig (20.8 MPa), preferably 2800 psig (19.4 MPa). The second reactive material, such as a polyisocyanate, will be simultaneously injected through valve 199 and conduit 200, convergent nozzle 201, in mixing head 196 and through exit chamber 198, thoroughly mixed with the material M (polyahl). When the mixing head is closed, both streams will be returned to their respective tanks via conduits 202 and 203.

A supply tank 262 is provided for the delivery of blowing agent via exit valve 263, pressure regulator 264, into line 265. Line 265 carries a pressure gauge 215, valve 216, mass flow meter 217, valve 218 and check valve 219 which feed the blowing agent to and through a series of spargers 220, positioned within the bottom of tank 261. The spargers are of a porosity to create minute gas bubbles or droplets having an average diameter of up to about 100 microns, preferably about 10 microns, more preferably about 1 micron and most preferably about 0.2 micron. Orientation of the spargers 220 is horizontal, rather than vertical, to cover a large area of the tank 261.

The apparatus 260 also provides for the recirculation of the liquid in line 183, through line 229 and heat exchanger 231. Upon leaving the heat exchanger, the liquid is fed through a separate sparger unit 232, which is fed blowing agent by line 233, diverted from line 265 and back into the tank 261. Additional, or fresh liquid material, via line 182, is also fed through that exchanger 231 and sparger unit 232, so as to minimize the effect of the fresh material on the operating conditions within tank 261, thereof. Contents of the tank are mixed in a conventional fashion by providing an agitator 237, driven by motor 238, and having blades 239.

When it is desired or necessary to measure the volumetric expansion potential of the mixture, the apparatus provides means for measuring, indicated generally by the numeral 240, which is an alternative embodiment to the first and second chambers as described hereinabove. Means for measuring 240 comprises an expansion cylinder 241, having a piston 242, movable by a cylinder 243 equipped with valves 244 and 245. A portion of the liquid is diverted from line 183 in a parallel side stream line 246. In actuality, a first chamber 250 is defined by the volume between valves 248 and 249 and the top of the piston 242 when the piston 242 is fully extended. A second chamber 251 is provided by the total fixed volume of the first chamber 250 added to the volume created by withdrawing piston 242 in expansion cylinder 241.

Pressure of the mixture is captured by transducer 252 and then piston 242 is withdrawn until the pressure within the chamber has fallen to the desired reduced pressure. At this point the length of travel of piston 242 is captured by transducer 253 and the expansion potential of the mixture is measured. After sampling is complete, the piston 242 is extended to recompress the sample; valves 249 and 248 are opened to allow the sample chamber to be purged.

Figure 5:
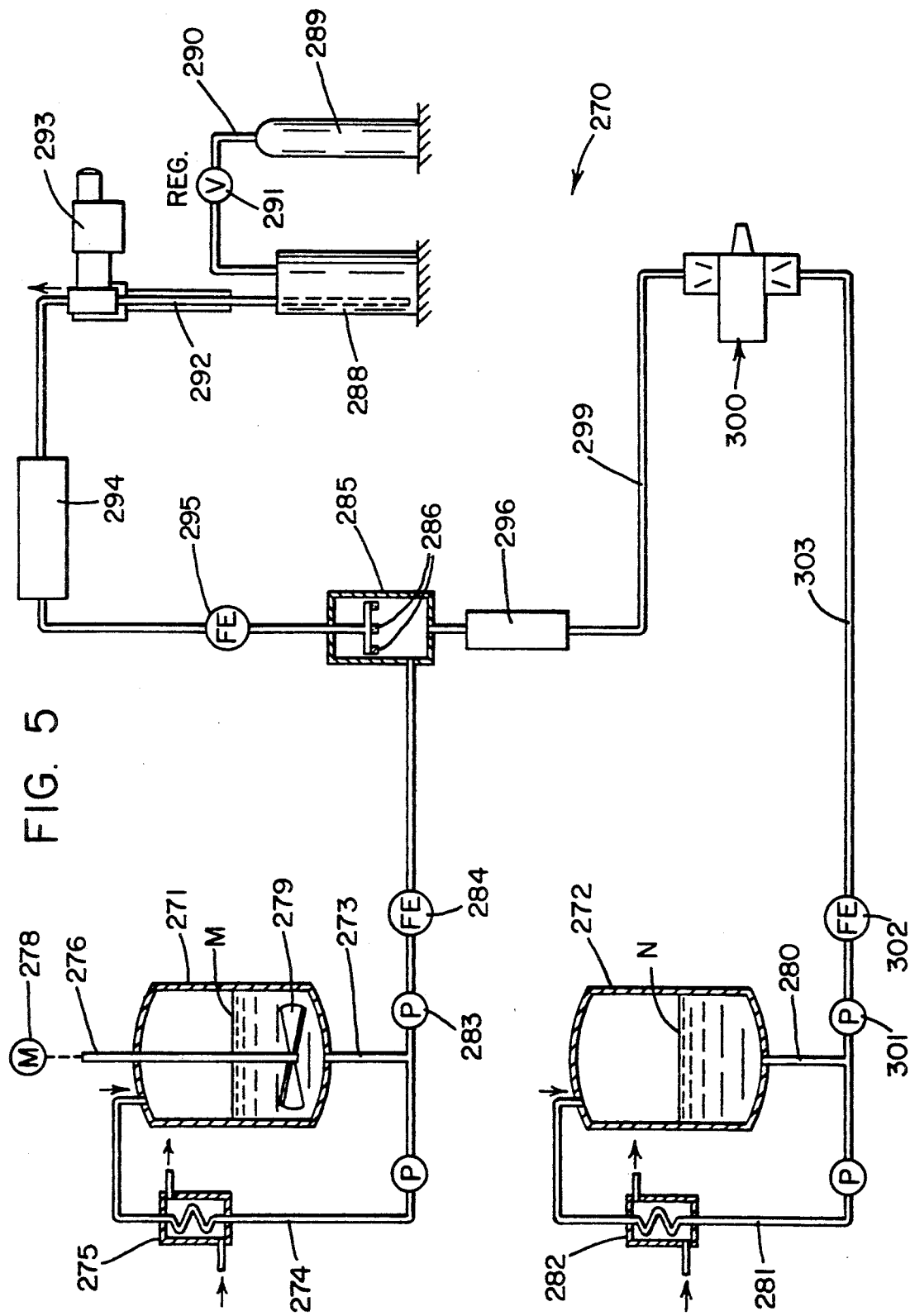
FIG. 5 is a schematic flow diagram of apparatus, according to the present invention, for incorporation of blowing agents into a liquid material employed for the continuous manufacture of polymer foams as typically utilized for bun line or laminator lines.

FIG. 5 illustrates an alternative embodiment and method for the incorporation of a blowing agent, into a liquid material which incorporates several essential features of the invention. The apparatus, referred to generally by the numeral 270, also employs a suitable digital control system, as described in conjunction with FIGS. 1 and 2 hereinabove. Again, because such control systems are well known and do not constitute novelty herein, no further description is deemed necessary. Apparatus 270 depicts a two component liquid material system, e.g., polyahl and isocyanate, for the manufacture of polyurethane. For purposes of discussion, apparatus 270 shall be described in conjunction with the addition of a blowing agent into the polyahl liquid, material component M, it being understood that one may wish to add the blowing agent to the isocyanate component or to both.

A liquid material holding and mixing tank 271 is provided for receipt of a supply of polyahl material M, while a similar tank 272 is provided for receipt of a supply of isocyanate material N. Tanks 271 and 272 are designed to withstand pressures of up to about 1000 psig (7.0 MPa) and are fed liquid materials from respective sources (not shown). Preferably the pressure within the tanks may be about 600 psig (4.1 MPa) and most preferably about 435 psig (3.0 MPa). It is to be understood that even higher pressures are not to be precluded, if a desired material and blowing agent combination may eventually require such pressure, and similarly, pressures as low as 0.0 psig (0.1 MPa) may be suitable with other combinations.

For the purpose of efficiency, the remainder of discussion shall be limited to introduction of blowing agent into polyahl, although it is not intended to limit the invention in this manner. It should be understood that blowing agent can be likewise added to other reactive liquid component.

Material M is recirculated through conduits 273 and 274 and heat exchanger 275 to maintain a constant temperature, while agitator 276, driven by motor 278, and providing blades 279, maintains uniformity in the mixture as new liquid is added. Similarly material N is recirculated through conduits 280 and 281 and heat exchanger 282 to maintain a constant temperature, and while no agitator is shown, it is to be understood that the contents of tank 272 could also be mixed as new liquid is added.

Delivery of material M is controlled via pump 283, through mass or positive displacement flow meter 284, to a sparger unit 285 where the blowing agent is introduced through spargers 286. The blowing agent is provided from a suitable source 288, in liquid or gaseous form. By this example, however, the blowing agent utilized is a liquified cryogenic gas in source 288. A supply of blowing agent or suitable compressed gas 289 is provided and fed to liquid source 288 via conduit 290, through a regulator 291 to force blowing agent from source 288. The liquid blowing agent is then fed through a jacketed refrigerated tube 292 and appropriate pump 293 for moving liquid. The liquid is next fed through a vaporizer 294 and finally through a mass flow meter 295 and into the sparger unit 285. Delivery rate of the blowing agent will be controlled by pump 293. Other suitable mass controlled blowing agent delivery systems as described hereinabove, may be used with or instead of the cryogenic supply system.

Upon exiting the sparger unit 285, the liquid/gas mixture is passed through a contactor 296 which is suitably controlled to provide adequate residence time and shearing action as can be experimentally determined for incorporation of the necessary amounts of blowing agent in the liquid component. The mixture of blowing agent and liquid material is then passed via line 299 into the mixhead 300 where it is combined with the second liquid component from tank 272 which is, in turn, fed via pump 301, through mass flow meter 302 and line 303.

As should now be apparent from the foregoing description, the apparatuses and methods for incorporating blowing agents provide a closed system in the sense that a pre-determined amount of blowing agent is delivered directly from a source, to the liquid mixture and then incorporated therein, without escape to the atmosphere. Understandably, to ensure incorporation of precise amounts of blowing agent, all conduits should be appropriately charged so that the desired blowing agent and amount thereof is actually delivered to the liquid material. In similar fashion, the apparatuses and methods for measuring the volumetric expansion also provide a closed system inasmuch as samples taken are tested without direct contact with the surrounding atmosphere or loss of blowing agent.

Thus it should be evident that the apparatuses and methods of the present invention provide a highly effective and accurate system for incorporating minute bubbles or droplets of at least one blowing agent into one or both liquid components of a two component reactive system for the manufacture of polymer foams, as well as for measuring the amount of volumetric expansion potential of a blowing agent/liquid material mixture. The invention is particularly suited for producing polyurethane foams and the use of low boiling blowing agents, but is not necessarily limited thereto. The apparatuses for incorporating and for measuring can be combined and used in the same overall system or, each can be used separately with other equipment, methods and the like, as well as for the manufacture of other polymer foams.

Regarding the latter, the apparatuses and methods of the present invention can also be employed separately or together with other liquid materials than employed to form polyurethanes, to which blowing agents are added to form polymer foams. Accordingly, while the present invention includes as the preferred embodiment a disclosure of polyurethane-forming liquid materials, the invention is not necessarily limited thereto.

Based upon the foregoing disclosure, it should now be apparent that the use of the apparatuses described herein will carry out the objects set forth hereinabove. It is, therefore, to be understood that any variations evident fall within the scope of the claimed invention and thus, the selection of specific component elements can be determined without departing from the spirit of the invention herein disclosed and described. Moreover, the scope of the invention shall include all modifications and variations that may fall within the scope of the attached claims.

What is claimed is:

1. Apparatus for incorporating blowing agents into a liquid material comprising:
   high pressure tank means containing a liquid material under pressure;
   means for delivering a pre-determined quantity of at least one blowing agent into said liquid material in minute bubbles or droplets having an average diameter of from about less than 0.2 micron up to about 100 microns; and
   means for uniformly incorporating said blowing agent throughout said liquid material.

2. Apparatus for incorporating blowing agents, as set forth in claim 1, wherein said means for delivering includes
   cylinder means providing a movable piston;
   means for moving said piston; and
   means for controlling the position of said piston between opened and closed positions.

3. Apparatus for incorporating blowing agents, as set forth in claim 2, wherein said means for delivering further includes
   means for controlling the temperature of said blowing agents within said cylinder means; and
   transducer means for monitoring the temperature and pressure of said blowing agent within said cylinder.

4. Apparatus for incorporating blowing agents, as set forth in claim 2, wherein said means for delivering further includes
   a plurality of spargers immersed within the liquid material to form said bubbles or droplets of blowing agent.

5. Apparatus for incorporating blowing agents, as set forth in claim 1, wherein said means for delivering includes
   a sparger unit carrying a plurality of spargers contacted by said liquid material flowing therethrough.

6. Apparatus for incorporating blowing agents, as set forth in claim 1, wherein said apparatus further includes
   means for monitoring the mass of said liquid material and said quantity of blowing agent.

7. Apparatus for incorporating blowing agents, as set forth in claim 1, wherein said means for incorporating comprises a contactor.

8. Apparatus for incorporating blowing agents, as set forth in claim 1, further comprising first means for metering the flow of blowing agent fed to said liquid material and second means for measuring a volume of blowing agent expelled from said liquid material.

9. Apparatus for measuring the volumetric expansion potential of a mixture of at least one blowing agent and a liquid material component within a closed system comprising:
   high pressure tank means containing liquid material and at least one blowing agent under pressure;
   means for measuring the volumetric expansion potential of said mixture, providing first and second chambers, communicating with each other and with said tank;
   means for transferring said mixture into and out of said first and second chambers, said second measuring chamber having a volume sufficiently greater than the volume of said first chamber whereby at least some of said blowing agent will leave said mixture;
   means for measuring the pressure in said first chamber; and
   means for measuring the volumes displaced by said mixture within said first and second chambers.

10. Apparatus for measuring the volumetric expansion potential of a mixture of blowing agent and liquid material, as set forth in claim 9, wherein said first chamber provides a piston communicating with said means for transferring and is movable between opened and closed positions and said second chamber provides a piston communicating with said means for transferring and is movable between opened and closed positions.

11. Apparatus for measuring the volumetric expansion potential of a mixture of blowing agent and liquid material, as set forth in claim 10, wherein said second chamber has a volume of from about less than one order of magnitude up to about three orders of magnitude greater than said first chamber.

12. Apparatus for measuring the volumetric expansion potential in a mixture of blowing agent and liquid material, as set forth in claim 10, further comprising
   conduit means connecting said first and second chambers whereby as said piston in said first chamber is moved to said closed position, said piston in said second chamber is moved to said opened position.

13. Apparatus for measuring the volumetric expansion potential of a mixture of blowing agent and liquid material, as set forth in claim 9, further including
   means for controlling the temperature within said first and second chambers; and
   transducer means for monitoring the temperature within said first and second chambers.

14. Apparatus for measuring the volumetric expansion potential of a mixture of blowing agent and liquid material, as set forth in claim 9, wherein said first chamber is defined by a closed volume, separating a pre-determined quantity of the mixture and said second chamber is defined by the expansion of said first chamber.

15. Apparatus for measuring the volumetric expansion potential of a mixture of blowing agent and liquid material, as set forth in claim 9, further comprising
   conduit means and valves for controllably feeding said means for measuring and providing a separate quantity of said mixture thereto.

16. Apparatus for measuring the volumetric expansion potential of a mixture of blowing agent and liquid material, as set forth in claim 15, wherein said means for measuring includes expandable cylinder means for receipt of a pre-determined quantity of said mixture, providing a movable piston, and said first chamber is defined by the volume within said cylinder means substantially closed and the volume within said conduit means up to said valves, and said second chamber is defined by the volume within said first chamber upon withdrawal of said piston.

17. Apparatus for measuring the volumetric expansion potential of a mixture of blowing agent and liquid material, as set forth in claim 9, wherein said means for measuring comprises
   first expandable cylinder means for receipt of a pre-determined quantity of said mixture, providing a movable piston;
   second expandable cylinder means providing a movable piston; and
   conduit means joining the interior of said first cylinder means with the interior of said second cylinder means,
   wherein said first chamber is defined by the volume within said first cylinder means substantially closed, the volume within said conduit means up to said valves and the volume within said second cylinder means substantially closed and,
   the volume of said second chamber is defined by the volume within said first chamber upon withdrawal of at least one of said pistons from their respective cylinders.

18. Apparatus for measuring the volumetric expansion potential of a mixture of blowing agent and liquid material, as set forth in claim 9, wherein said pressure in said tank means ranges from at least about 0.0 psig (0.1 MPa) up to about 1000 psig (7.0 MPa)

19. A method for the incorporation of blowing agents into a liquid material comprising the steps of:
   feeding a pre-determined amount of liquid material to a supply tank;
   supplying a pre-determined amount of at least one blowing agent to said supply tank through means immersed within said liquid material to produce bubbles or droplets having an average diameter of from about less than 0.2 micron up to about 100 microns.

20. A method, as set forth in claim 19, including the additional step of
   raising the pressure in said supply tank to a range of from at least about 50 psig (0.4 MPa) up to about 1000 psig (7.0 MPa) prior to said step of supplying.

21. A method, as set forth in claim 19, wherein said means immersed within said liquid material comprises a plurality of spargers.

22. A method, as set forth in claim 19, including the additional steps of
   monitoring the mass of said liquid material;
   monitoring the mass of said blowing agent introduced;
   monitoring the mass of said blowing agent escaping from said supply tank.

23. A method, as set forth in claim 19, wherein said step of supplying a blowing agent includes the step of employing an agent selected from the group consisting of gases and liquids, soluble and insoluble in said liquid material, and mixtures thereof, and said liquid material is selected from the group consisting of polymers employed for the production of polymer foams.

24. A method, as set forth in claim 23, wherein said blowing agent is selected from the group consisting of chlorofluorcarbons, hydrochlorofluorocarbons, perfluoroalkanes, hydrofluoroalkanes, normal and branched alkanes, esters, ethers, noble gases, ammonia, pentane and isomers thereof, water, steam, carbon dioxide, helium, nitrogen and air and mixtures thereof and said liquid material is selected from the group consisting of polyahls and polyisocyanates.

25. A method, as set forth in claim 19, wherein said step of supplying a blowing agent includes the steps of
   supplying said pre-determined volume of at least one blowing agent to a cylinder for injection into said supply tank;
   pressurizing said blowing agent in said cylinder;
   delivering said blowing agent from said cylinder to said supply tank through means located in said tank to produce bubbles or droplets.

26. A method, as set forth in claim 19, including the additional step of
   providing said liquid material and blowing agent to a contactor to incorporate said blowing agent into said mixture.

27. A method for measuring the volumetric expansion potential of a mixture of at least one blowing agent and a liquid material within a closed system comprising the steps of:
   withdrawing a quantity of said mixture from a supply tank;
   feeding said quantity into a first chamber under pressure;
   allowing expansion of said quantity within said first chamber to a volume sufficiently greater to cause at least some of said blowing agent to leave said mixture; and
   thereby measuring the amount of blowing agent in said mixture.

28. A method, as set forth in claim 27, wherein said step of feeding includes the steps of
   withdrawing a piston in said first chamber a pre-determined distance to form a cavity therein for said quantity; and
   controlling the position of said piston between limits to define opened and closed positions of said first chamber.

29. A method, as set forth in claim 27, including the additional step of controlling the temperature of the liquid material in said first chamber.

30. A method, as set forth in claim 27, including the additional steps of
provide a second chamber having a movable piston and means for communicating between said first and second chambers;
withdrawing said piston in said second chamber a distance to form a cavity;
expanding at least some of said mixture within said cavity to allow at least some of the blowing agent in said mixture to leave said mixture; and
controlling the position of said second chamber piston between limits to define opened and closed positions of said second chamber.

31. A method, as set forth in claim 27, wherein the pressure on said liquid material/blowing agent mixture in said tank and said first chamber ranges from at least about 0 psig (0.1 MPa) up to about 1000 psig (7.0 MPa) and the pressure in said second chamber can be varied from about 1000 psig (7.0 MPa) to less than atmospheric, depending on the liquid material mixture being measured.

32. A method, as set forth in claim 27, wherein said step of supplying a blowing agent includes the step of employing an agent selected from the group consisting of gases and liquids, soluble and insoluble in said liquid material, and mixtures thereof, and said liquid material is selected from the group consisting of polymers employed for the production of polymer foam.

33. A method, as set forth in claim 32, wherein said blowing agent is selected from the group consisting of chlorofluorocarbons, hydrochlorofluorocarbons, perfluoroalkanes, hydrofluoroalkanes, normal and branched alkanes, esters, ethers, noble gases, ammonia, pentane and isomers thereof, water, steam, carbon dioxide, helium, nitrogen and air and mixtures thereof and said liquid material is selected from the group consisting of polyahls and polyisocyanates.

34. Apparatus for incorporating blowing agents into a liquid material and measuring the volumetric expansion potential of a mixture thereof within a closed system comprising:
high pressure tank means containing a liquid material under pressure;
means for delivering a pre-determined quantity of at least one blowing agent into said liquid material in minute bubbles or droplets having an average diameter of from about less than 0.2 micron up to about 100 microns;
means for uniformly distributing said blowing agent throughout said liquid material; and
means for measuring the volumetric expansion potential of said mixture outside of said tank, providing first and second chambers.

35. Apparatus for incorporating blowing agents into a liquid material and measuring the volumetric expansion potential of a mixture thereof, as set forth in claim 34, wherein said first and second chambers communicate with each other and with said tank; and said apparatus further includes
means for transferring said mixture into and out of said first and second chambers, said second measuring chamber having a volume sufficiently greater than the volume of said first chamber whereby at least some of said blowing agent will leave said mixture;
means for measuring the pressure in said first chamber; and
means for measuring the volumes displaced by said mixture within said first and second chambers.

36. Apparatus for measuring the volumetric expansion potential of a mixture of blowing agent and liquid material, as set forth in claim 34, wherein said first chamber provides a piston communicating with said means for transferring and is movable between opened and closed positions and said second chamber provides a piston communicating with said means for transferring and is movable between opened and closed positions.

37. Apparatus for measuring the volumetric expansion potential of a mixture of blowing agent and liquid material, as set forth in claim 34, wherein said second chamber has a volume of from about less than one order of magnitude up to about three orders of magnitude greater than said first chamber.

38. Apparatus for measuring the volumetric expansion potential in a mixture of blowing agent and liquid material, as set forth in claim 36, further comprising
conduit means connecting said first and second chambers whereby as said piston in said first chamber is moved to said closed position, said piston in said second chamber is moved to said opened position.

39. Apparatus for measuring the volumetric expansion potential of a mixture of blowing agent and liquid material, as set forth in claim 34, further including
means for controlling the temperature within said first and second chambers; and
transducer means for monitoring the temperature within said first and second chambers.

40. Apparatus for measuring the volumetric expansion potential of a mixture of blowing agent and liquid material, as set forth in claim 34, wherein said first chamber is defined by a closed volume, separating a pre-determined quantity of the mixture and said second chamber is defined by the expansion of said first chamber.

41. Apparatus for measuring the volumetric expansion potential of a mixture of blowing agent and liquid material, as set forth in claim 34, further comprising
conduit means and valves for controllably feeding said means for measuring and providing a separate quantity of said mixture thereto.

42. Apparatus for measuring the volumetric expansion potential of a mixture of blowing agent and liquid material, as set forth in claim 41, wherein said means for measuring includes expandable cylinder means for receipt of a pre-determined quantity of said mixture, providing a movable piston, and said first chamber is defined by the volume within said cylinder means substantially closed and the volume within said conduit means up to said valves, and said second chamber is defined by the volume within said first chamber upon withdrawal of said piston.

43. Apparatus for measuring the volumetric expansion potential of a mixture of blowing agent and liquid material, as set forth in claim 34, wherein said means for measuring comprises
first expandable cylinder means for receipt of a pre-determined quantity of said mixture, providing a movable piston;
second expandable cylinder means providing a movable piston; and conduit means joining the interior of said first cylinder means with the interior of said second cylinder means, wherein said first chamber is defined by the volume within said first cylinder means substantially closed, the volume within said conduit means up to said valves and the volume within said second cylinder means substantially closed and.

the volume of said second chamber is defined by the volume within said first chamber upon withdrawal of at least one of said pistons from their respective cylinders.

* * * * *